United States Patent [19]
Ries

[11] Patent Number: 4,837,283
[45] Date of Patent: Jun. 6, 1989

[54] MONOMERIC, OLIGOMERIC AND POLYMERIC SULFONATES

[75] Inventor: Donald G. Ries, Richmond, Tex.

[73] Assignee: Nalco Chemical Company, Naperville, Ill.

[21] Appl. No.: 90,850

[22] Filed: Aug. 31, 1987

[51] Int. Cl.$^4$ ............................................. C08G 65/32
[52] U.S. Cl. .................................. 525/403; 528/391; 260/508; 260/510; 260/512 R; 260/513 R; 260/513 N
[58] Field of Search ....................... 525/403; 528/391; 260/508, 510, 512 R, 513 R, 513 N

[56] References Cited

U.S. PATENT DOCUMENTS

| 2,861,101 | 11/1958 | Tousignant | 260/513 |
| 3,305,565 | 2/1967 | Mueller | 528/408 X |
| 4,379,872 | 4/1983 | Ishikura et al. | 528/391 X |
| 4,436,672 | 3/1984 | Naylor | 260/512 R |
| 4,574,061 | 3/1986 | Ries | 260/512 |

OTHER PUBLICATIONS

Chemical Abstracts, vol. 55, 21628.
"Chemical Modification of Poly(1-chloro-2-epoxypropane) Using Phase Transfer Catalysis" Makromol. Chem. Rapid Comm. 3, 617–622 (1982).

Primary Examiner—Earl Nielsen
Attorney, Agent, or Firm—Arnold, White & Durkee

[57] ABSTRACT

Monomeric, oligomeric and polymeric sulfonates are formed by the reaction of a compound containing at least one epihalohydrin residue and a sulfonate compound selected from the group consisting of phenolsulfonic acid salts, naphtholsulfonic acid salts, aminobenzene sulfonic acid salts and aminoalkyl sulfonic acid salts.

23 Claims, No Drawings

MONOMERIC, OLIGOMERIC AND POLYMERIC SULFONATES

FIELD OF THE INVENTION

This invention is directed to novel surfactants. More specifically, the invention is directed to monomeric, oligomeric and polymeric sulfonates having pendant sulfonate groups depending from glycol moiety.

BACKGROUND OF THE INVENTION

Anionic surfactants are useful in a variety of applications. Most common among the anionic surfactants are the sulfates and sulfonates. In applications involving extremes of pH and/or high temperatures, sulfonates are preferred over sulfates due to their greater thermal and hydrolytic stability.

Sulfonates are generally prepared by the reaction of $SO_3$ with hydrocarbon acceptors such as alkenes and arenes. Conventional sulfonate surfactants are typified by the petroleum sulfonates and alkylaryl sulfonates such as dodecylbenzene sulfonates.

Polymers containing multiple sulfonate groups are known. Typically, such polymers are prepared by the copolymerization of vinylic sulfonic acid monomers, such as 4-styrene sulfonic acid with other vinyl monomers. The relative high cost of vinylic sulfonate monomers has limited their use in surfactant applications.

In U.S. Pat. No. 4,574,061, alkoxyaryl sulfonates having up to five repeating aryl sulfonate units per molecule are disclosed. The sulfonates are represented by the general formula:

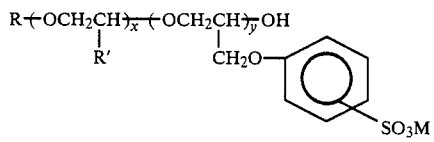

wherein R is a $C_6$–$C_{20}$ hydrocarbon or substituted hydrocarbon group, R' is from the group consisting of hydrogen and lower alkyl of from one to four carbon atoms, x is an integer having a value between 0 and 50 and y is an integer within the range of 1 to 5. These alkoxyaryl sulfonates are prepared by the reaction of an epihalohydrin capped alcohol or alkoxylated alcohol with phenolsulfonic acid.

U.S. Pat. No. 2,861,101 discloses polysulfonic acid polymers. The disclosed compounds are prepared by reacting polyepichlorohydrin with an alkali metal sulfite salt. The polyepichlorohydrin disclosed was polymerized using propylene glycol as the oxide acceptor or initiator. The compounds disclosed in this patent can be represented by the general formula:

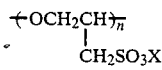

wherein n is a plural integer and X is hydrogen or a salt-forming cation.

The reaction of phenol with an epihalohydrin is disclosed in Makromol. Chem. Rapid Comm., 3, 617-622 (1982); (CA 97,145413). The disclosed reaction may be represented by the following formula:

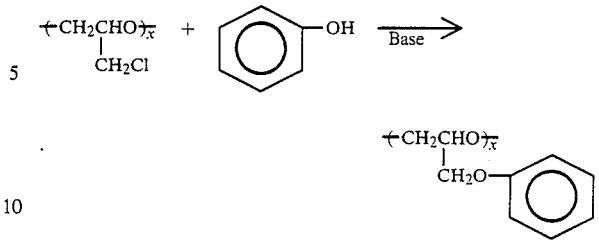

An additional reaction of a phenolic compound with polyepichlorohydrin is disclosed in Japanese Patent No. 73 03707 (CA 80,27723). This reaction can be represented by the following formula:

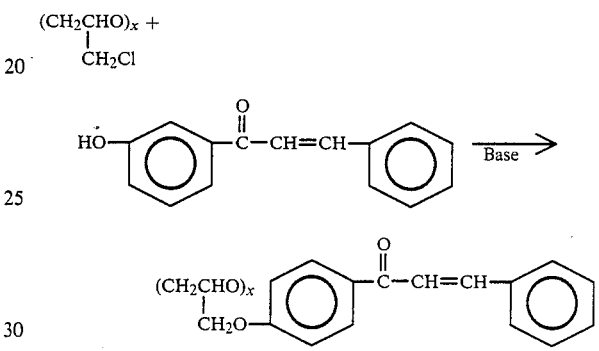

Surface active compounds (e.g., Na N-(1-dodecyloxy-2-hydroxy propyl)-N-methylaminoethane sulfonate) are disclosed in CA 55, 21628. These compounds are prepared from glycidyl ethers and amino sulfonates (e.g., Na methylaminoethane sulfonate or Na aminobenzene sulfonate).

SUMMARY OF THE INVENTION

The present invention comprises oligomeric and polymeric sulfonates comprising the reaction product of a polymer having at least one polyglycol segment containing epihalohydrin residue units and a sulfonate compound selected from the group consisting of phenolsulfonic acid salts, naphtholsulfonic acid salts, aminobenzene sulfonic acid salts and aminoalkyl sulfonic acid salts.

The invention also comprises surfactants comprising the reaction product of a compound having at least one epihalohydrin residue and a sulfonate compound selected from the group consisting of sulfanilic acid salts and aminoalkyl sulfonate salts.

DETAILED DESCRIPTION

Definitions

"Polyglycol segment" is used to refer to oligomeric or polymeric molecules or segments of molecules characterized by the general structure

The carbons of this generalized structure may be substituted with alkyl, aryl, and halogen groups.

"Oxirane compound" refers to compounds characterized by the presence of a three membered oxygen containing heterocyclic ring. Typical oxirane compounds include ethylene oxide and epichlorohydrin.

"Epihalohydrin" refers to compounds having the general structure

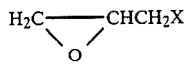

where X is halogen. Epichlorohydrin and epibromohydrin are the most useful epihalohydrins. As epichlorohydrin is the most common, the following description and examples will be made in reference to epichlorohydrin. By doing so, there is no intent to limit the invention to compounds utilizing it as a starting material.

"Epihalohydrin residue" is defined as the moiety

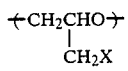

wherein X is halogen.

"Epihalohydrin residue compound" is defined as a molecule having at least one epihalohydrin residue.

"Oxide acceptor" refers to compounds having functional groups such as hydroxyl groups reactive with an oxirane compound.

"Polyol acceptor" refers to compounds having multiple functional groups reactive with an oxirane compound. Typical polyol acceptors include ethylene glycol and glycerin.

"Lower alkyl" refers to alkyl groups of from 1 to 4 carbon atoms.

GENERALIZED PROCESS

The sulfonates of the instant invention are produced by the reaction of a compound having at least one epichlorohydrin residue with a sulfonate compound selected from the group consisting of phenolsulfonic acid salts, naphtholsulfonic acid salts, aminobenzene sulfonic acid salts and aminoalkyl sulfonic acid salts.

EPICHLOROHYDRIN RESIDUE COMPOUNDS

Compounds containing epichlorohydrin residues are prepared by the reaction of epichlorohydrin with a suitable oxide acceptor. As will be described below, such compounds may contain one or many epichlorohydrin residue units. For example, an alcohol such as n-hexanol can be reacted with a single equivalent of epichlorohydrin to produce a compound having one epichlorohydrin residue. This compound can then be reacted with a sulfonate compound to produce a surfactant sulfonate. Alternatively, the alcohol could be reacted with more than one equivalent to produce a molecule have multiple epichlorohydrin residue units in a polyglycol segment. This compound could then be reacted with a sulfonate compound to produce a polymeric sulfonate.

Polyglycol Segment

Molecules having polyglycol segments can take a variety of forms. The simplest and preferred form is a molecule having a single polyglycol segment. Most preferred of such compounds is polyepichlorohydrin. Polyepichlorohydrin is easily prepared by the reaction of epichlorohydrin with water in the presence of a catalyst. Continued addition of epichlorohydrin to the reaction results in the formation of a polymer of the general formula

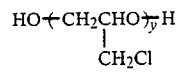

wherein y is an integer of more than 1 and typically less than about 50. Polymers where y is in the range of 5 to 20 are preferred. As is known in the art, the molecular weight of the polymer can be controlled by varying the ratio of epichlorohydrin to the acceptor (water).

The formation of polyepichlorohydrin is well known and, for use in this invention, the method of preparation is not critical. Generally, Lewis acids are used as catalysts. $BF_3$-ethyl etherate is the preferred catalyst. Reaction rate and temperature are controlled by rate of addition of epichlorohydrin and cooling and/or heating as necessary.

Alternatively, an oxide acceptor other than water can be used to initiate the polyepichlorohydrin chain. In general, compounds possessing labile hydrogens such as phenolic and alcoholic hydroxyls are suitable acceptors. Other potential acceptors include carboxylic acids. Amines, while well known as oxide acceptors, are not suitable for use in this invention due to their reactivity with halogenated hydrocarbons such as epichlorohydrin.

Typical alcoholic acceptors include linear and branched aliphatic alcohols having from 1 to about 20 carbon atoms. Typical phenolic acceptors include phenol and substituted phenols. Both the alcohols and phenols can be alkoxylated prior to reaction with epichlorohydrin. In the case of substituted phenols, suitable substituants include alkyl groups, aryl groups and alkylaryl groups of from 1 to about 20 carbon atoms. Examples of such compounds include butylphenol, octylphenol, amylphenol, nonylphenol, dodecylphenol, phenylphenol and cumylphenol. Other suitable phenolic acceptors include naphthol and substituted naphthols. Polyepichlorohydrin prepared using such acceptors or water would have the general formula

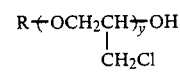

wherein R is H, a $C_1$ to $C_{20}$ alkyl or alkaryl group and y is defined as above. In many surfactant applications, hydrocarbon groups of 6 to 20 carbon atoms will be most useful.

Another group of potential acceptors are polyols, i.e., compounds having multiple acceptor functional groups. One group of such compounds is represented by the alkyldiols of 2 to 6 carbon atoms. Illustrative of such compounds are ethylene glycol, propolyene glycol, glycerin, trimethylolpropane and sorbitol. Phenolic polyol compounds suitable as acceptors include resorcinol, bisphenol A and dimer, trimer and higher oligomers of phenol formaldehyde resins. These phenolic compounds can also be substituted as described above.

The polyglycol segment as well as being a polymer of epichlorohydrin can also be a copolymer or terpolymer of epichlorohydrin and other oxirane compounds. Suitable oxirane compounds include ethylene oxide, propylyene oxide, 1,2 butylene oxide, 2,3 butylene oxide and styrene oxide.

The copolymer can be a block or random copolymer. Block copolymers are prepared, for example, by reacting first one monomer, such as ethylene oxide, and then subsequently adding the second monomer, epichlorohydrin. The process can be repeated resulting in alternating blocks of epichlorohydrin and comonomer along the polyglycol backbone. Random copolymers can be prepared by mixing the monomers prior to introducing the monomer feed into the reactor. Such mixing results in an essentially random arrangement of monomer units along the polyglycol chain, assuming the relative rates of reaction of the two monomers are roughly equal.

Using the same starting materials and procedures just outlined, compounds containing a single epichlorohydrin residue can be formed. Obviously, by the addition of more than one equivalent of epichlorohydrin, molecules containing two, three or more residue units can be prepared. As described above, the methods of reacting epichlorohydrin with the acceptor are well known. The addition of co-oxirane compounds can also be carried out as previously described. The preparation of such alcohol-epichlorohydrin adducts is further described in U.S. Pat. No. 4,574,061 which is hereby incorporated by reference.

SULFONATE COMPOUNDS

The epichlorohydrin residue compound is next converted into a sulfonate by reaction with a sulfonate compound selected from the group consisting of phenolsulfonic acid salts, naphtholsulfonic acid salts, aminobenzene sulfonic acid salts and aminoalkyl sulfonic acid salts. These reactions may be represented a follows:

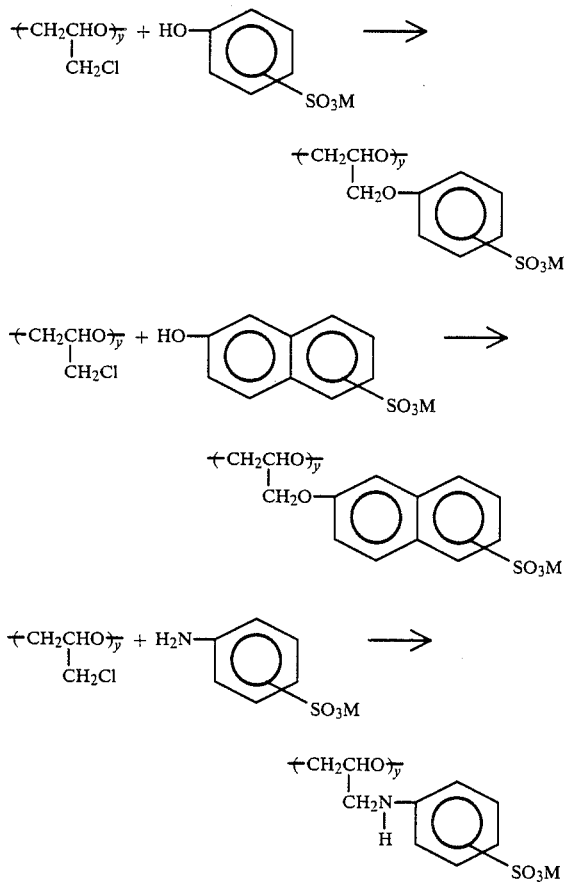

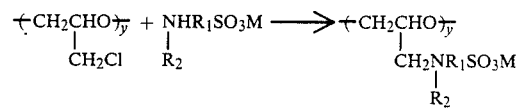

In addition to the phenolsulfonic acid salts, the naphtholsulfonic acid salts and the aminobenzene sulfonic acid salts, substituted variations of these can also be used. Any of the isomers can be utilized. In the case of phenolsulfonic acid, the para isomer is preferred. Sulfanilic acid is the preferred aminobenzene sulfonic acid.

Suitable aminoalkyl sulfonic acid salts include compounds of the formula

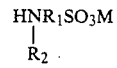

wherein $R_1$ is an alkyl group of 1 to about 20 carbon atoms and $R_2$ is H or alkyl of 1 to 4 carbon atoms and M is a suitable salt forming cation. Preferred among the aminoalkyl sulfonates are salts of 2-aminoethane sulfonic acid (taurine) and N substituted taurine (e.g., N-methyl taurine).

Suitable cations for the sulfonate salts are the metal cations. Ammonium ion is not suitable due to its reactivity with organic halogens. However, once the reaction of the epichorohydrin residue compound and the sulfonate has taken place, the sulfonate can be converted to the ammonium salt. Preferred cations are monovalent metals. Particularly preferred are the alkali metals sodium and potassium.

REACTION OF THE POLYGLYCOL BACKBONE AND THE SULFONATE COMPOUND

The reaction between the epichlorohydrin residue compound and the sulfonate compound is carried out in the presence of a base. The amount of sulfonate compound used should be sufficient to react on a one to one basis with the epichlorohydrin residue compound based on its chloride equivalency. The amount of base, assuming the reaction is started using a sulfonate salt rather than a sulfonic acid, is one equivalent of base per equivalent of sulfonate compound. If the starting compound is a sulfonic acid, an additional equivalent of base is necessary. Suitable bases include NaOH, KaOH, Na$_2$CO$_3$ and K$_2$CO$_3$. Preferably, a small amount of iodide salt such as NaI or KI is added to the reaction.

The reaction is carried out in a polar solvent system. Although water can be used alone, an alcohol water mixture such as isopropanol/water is preferred. Aprotic polar solvents such as DMF and DMSO can be used.

After mixing the reactants together, they are heated at a temperature and for a time sufficient to complete the reaction. Typical reaction temperatures are from about 90° C. to about 150° C. Reaction times typically vary from about five hours to about twenty hours. As water and/or alcohol is usually present in the solvent system, the use of a pressurized reaction vessel is indicated for the higher temperatures.

Typical Sulfonates

As can be appreciated from the foregoing description, a variety of different sulfonates within the scope of the present invention can be synthesized. The following generalized formulas are presented to aid in understanding the invention and are not intended to be an exhaustive listing of the structures encompassed by the invention.

Polymeric sulfonates prepared from polyepichlorohydrin can be represented as

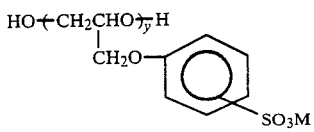

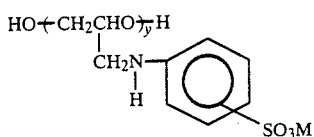

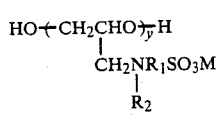

wherein y is an integer of more than 1 and typically less than about 50, M is a suitable salt forming cation, $R_1$ is an alkyl group of 1 to about 20 carbon atoms and $R_2$ is H or lower alkyl. Preferably y will be in the range of about 5 to about 20.

Additional polymeric sulfonates can be represented by the formula

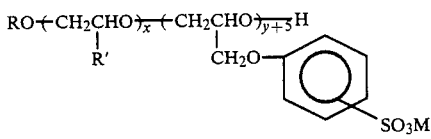

wherein R is H, an alkyl or an alkylaryl group of from 1 to about 20 carbon atoms, R' is H, lower alkyl or phenyl, x is an integer having a value from 0 to typically about 50, y is an integer of more than 1 and typically less than 50, and M is a suitable salt forming cation.

Monomeric, oligomeric and polymeric sulfonates can be represented by the formulae:

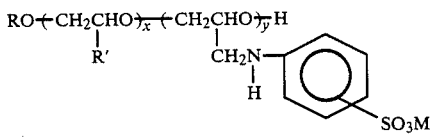

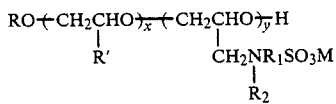

wherein R, R', $R_1$, $R_2$, M, x and y are as defined above.

EXAMPLES

Example One Preparation of Polyepichlorohydrin: Water Acceptor

A 500 ml four neck flask equipped with addition funnel, stirrer, thermometer and condenser is purged with nitrogen. 9 grams (0.5 moles) deionized water and 1 ml. $BF_3$-ether complex was then added. The temperature was raised to about 50° C. and 231 grams (2.5 moles) epichlorohydrin was added over one hour. The temperature climbed to 90° and was maintained by addition rate and cooling as necessary. After addition was completed, the temperature was maintained at 80° to 90°C. for an additional hour. After standing at room temperature for several days, the product was heated to 100° to 110° C. while purging with nitrogen for about two hours. The product was then cooled to yield 236 grams of polyepichlorohydrin.

Example Two

Preparation of Polyepichlorohydrin: Ethylene Glycol Acceptor

A 500 ml flask equipped with addition funnel, stirrer, thermometer and condenser is purged with nitrogen. 31 grams (0.5 mole) ethylene glycol and .5 ml $BF_3$ ether complex was then added. After heating to 45° C., 324 grams (3.5 moles) epichlorohydrin was added over a four hour period. During addition, the temperature climbed to 90° C. and was maintained at 90° C. or lower by cooling. After the addition was completed, the temperature was maintained at 90° C. for an additional three and one-half hours. After standing at room temperature, the product was heated to 110° C. for two hours while purging with nitrogen. On cooling, 344 grams of polyepichlorohydrin was recovered.

Example Three

Reaction of Polyepichlorohydrin With Phenol Sulfonic Acid

To a 600 ml PARR autoclave 37.3 grams (0.39 equivalents) of a polyepichlorohydrin made from one mole water and seven moles epichlorohydrin, 105.2 grams 65% phenol sulfonic acid solution, 65.9 grams 50% sodium hydroxide, 0.2 grams sodium iodide, 65 grams isopropanol, and 126.4 grams deionized water were charged. The autoclave was sealed and heated with stirring at 120° C. for six hours to give the product as a 25% active solution.

Example Four

Reaction of Polyepichlorohydrin With Phenol Sulfonic Acid

To a 600 ml PARR autoclave 41 grams (0.37 equivalents) of a polyepichlorohydrin prepared from one mole glycerin and 5 moles epichlorohydrin, 99 grams 65% phenol sulfonic acid, 62 grams 50% sodium hydroxide, 0.2 grams sodium iodide, 50 grams isopropanol and 147.8 grams deionized water were charged. The autoclave was sealed and heated with stirring at 125° C. for seven hours to give the product as a 25% solution.

Example Five

Reaction of Polyepichlorohydrin With Phenol Sulfonic Acid

To a 600 ml PARR autoclave 37.4 grams (0.39 equivalents) of a polyepichlorohydrin from one mole ethylene glycol and 20 moles epichlorohydrin, 105 grams 65% phenol sulfonic acid, 65.8 gram 50% sodium hydroxide, 0.2 grams sodium iodide, 65 grams isopropanol and 126.6 grams deionized water were charged. The autoclave was sealed and heated with stirring at 125° C. for seven hours. The product, which separated into two phases on cooling, was transferred to a rotary evaporator to remove the isopropanol under vacuum. Deionized water was then added to replace removed solvent to give the product as a 25% active solution.

Example Six

Reaction of Polyepichlorohydrin With Sulfanilic Acid

To a 600 ml PARR autoclave 40.2 grams (0.42 equivalents) polyepichlorohydrin from one mole water and five moles epichlorohydrin, 65.2 grams sulfanilic acid, 40 grams sodium carbonate, 0.2 grams sodium iodide and 254.6 grams deionized water were added. The autoclave was sealed and heated with stirring to 125° C. for a total of fourteen hours. The reactor was cooled and vented and deionized water was added to replace weight lost as carbon dioxide to give the product as a 25% active solution.

Example Seven

Reaction of Polyepichlorohydrin With N-methyltaurine

To a 600 ml PARR autoclave 32.7 grams (0.34 equivalents) of a polyepichlorohydrin from one mole water and five moles epichlorohydrin, 84.4 grams N-methyltaurine sodium salt (GAF Corporation N-methyltaurine 55), 27.2 grams 50% sodium hydroxide, 0.2 grams sodium iodide, 50 grams iosopropanol and 105.5 grams deionized water were charged. The autoclave was sealed and stirred at 100° C. for seven hours to give the product as a 25% active solution.

Example Eight

Reaction of Polyepichlorohydrin With N-methyltaurine

To a 600 ml PARR autoclave 32.5 grams (0.34 equivalents) of a polyepichlorohydrin from one mole ethylene glycol and 20 moles epichlorohydrin, 84.4 grams N-methyltaurine sodium salt, 27 grams 50% sodium hydroxide, 0.2 grams sodium iodide, 25 grams iosopropanol and 130.9 grams deionized water were charged. The autoclave was sealed and heated with stirring at 100° C. for seven hours to give the product as a 25% active solution.

The novel sulfonate according to the invention exhibit a variety of surfactant properties. As one skilled in the art will recognize, by varying the molecular weight and the balance of hydrophilic and lipophilic moieties, the surfactant properties can be tailored to suit specific needs. Included among potential uses of the novel sulfonates of the invention are, for example, use as emulsifiers, emulsion breakers, detergents and dispersants.

What is claimed is:

1. A polymeric sulfonate comprising the reaction product of a polyepihalohydrin and a compound selected from the group consisting of aminobenzene sulfonic acid salts and aminoalkyl sulfonic acid salts.

2. The polymeric sulfonate of claim 1 having the structural formula:

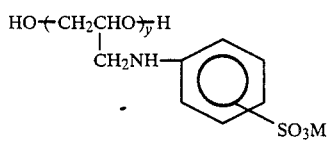

wherein y is an integer of more than 1 and M is a suitable salt forming cation.

3. The polymeric sulfonate of claim 2 wherein said aminobenzene sulfonic acid salt is a sulfanilic acid salt.

4. The polymeric sulfonate of claim 2 wherein y is greater than about 5 and less than about 50.

5. The polymeric sulfonate of claim 2 wherein M is selected from the group consisting of sodium and potassium.

6. The polymeric sulfonate of claim 1 having the structural formula:

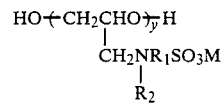

wherein y is an integer greater than 1, M is a suitable salt forming cation, $R_2$ is H or lower alkyl and $R_1$ is alkyl of $C_1$–$C_{20}$.

7. The polymeric sulfonate of claim 6 wherein y is greater than about 5 and less than about 50.

8. The polymeric sulfonate of claim 6 wherein $R_2$ is methyl and $R_1$ is ethyl.

9. The polymeric sulfonate of claim 6 wherein M is selected from the group consisting of sodium and potassium.

10. A sulfonate comprising the reaction product of a compound having at least one epihalohydrin residue and a compound selected from the group consisting of aminobenzene sulfonic acid salts and aminoalkyl sulfonic acid salts.

11. The sulfonate of claim 10 having the structural formula:

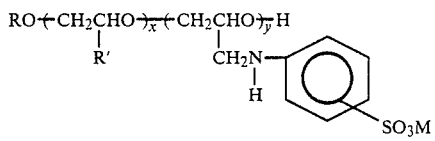

wherein R is H, a $C_1$–$C_{20}$ alkyl or alkylaryl group, R' is H, lower alkyl or phenyl, x is an integer having a value from 0 to about 50, y is an integer having a value from 1 to about 50, and M is a suitable salt forming cation.

12. The sulfonate of claim 11 wherein said aminobenzene sulfonic acid is a sulfanilic acid salt.

13. The sulfonate of claim 11 wherein R' is H or methyl.

14. The sulfonate of claim 11 wherein said

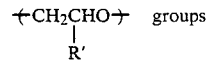 groups and said

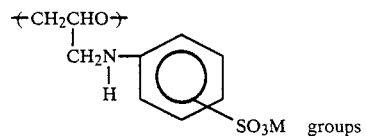 groups are arranged in blocks.

15. The sulfonate of claim 11 wherein said

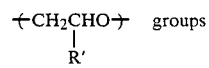 groups and said

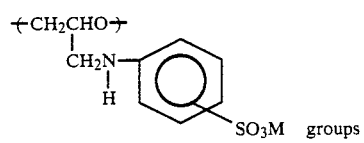

are arranged randomly.

16. The sulfonate of claim 11 wherein x is from 0 to about 20, and y is in the range of 1 to about 5.

17. The sulfonate of claim 16 wherein M is selected from the group consisting of sodium and potassium.

18. The sulfonate of claim 10 having the structural formula:

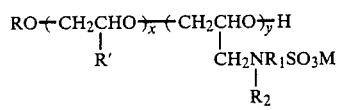

wherein R is H, a $C_1$–$C_{20}$ alkyl or alkylaryl group, R′ is H, lower alkyl, or phenyl, $R_2$ is H or lower alkyl, $R_1$ is a $C_1$–$C_{20}$ alkyl group, M is a suitable salt forming cation, x is an integer having a value from 0 to 50 and y is an integer having a value from 1 to about 50.

19. The sulfonate of claim 18 wherein R′ is H or methyl.

20. The sulfonate of claim 18 wherein said

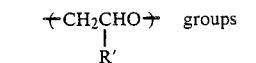

and said

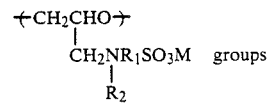

are arranged in blocks.

21. The sulfonate of claim 18 wherein said

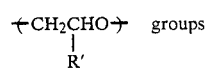

and said

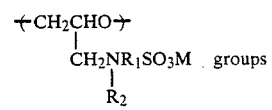

are arranged randomly.

22. The sulfonate of claim 18 wherein x is within the range of 0 to about 20, and y is in the range of 1 to about 5.

23. The sulfonate of claim 22 wherein M is sodium or potassium.

* * * * *